(12) United States Patent
Eggenweiler et al.

(10) Patent No.: US 7,019,013 B2
(45) Date of Patent: Mar. 28, 2006

(54) SULFAMIDOTHIENOPYRIMIDINES

(75) Inventors: Hans-Michael Eggenweiler, Weiterstadt (DE); Harry Schwartz, Hofheim (DE); Pierre Schelling, Muehltal (DE); Norbert Beier, Reinheim (DE); Maria Christadler, Roedermark (DE)

(73) Assignee: Merck Patent GmbH, Darmstadt (DE)

( * ) Notice: Subject to any disclaimer, the term of this patent is extended or adjusted under 35 U.S.C. 154(b) by 52 days.

(21) Appl. No.: 10/451,183

(22) PCT Filed: Dec. 3, 2001

(86) PCT No.: PCT/EP01/14102

§ 371 (c)(1),
(2), (4) Date: Jun. 20, 2003

(87) PCT Pub. No.: WO02/051848

PCT Pub. Date: Jul. 4, 2002

(65) Prior Publication Data

US 2004/0063943 A1    Apr. 1, 2004

(30) Foreign Application Priority Data

Dec. 23, 2000   (DE) .................. 100 64 994

(51) Int. Cl.
*C07D 495/04*   (2006.01)
*A61K 31/519*   (2006.01)
*A61P 9/00*   (2006.01)
*A61P 15/10*   (2006.01)

(52) U.S. Cl. ..................... 514/267; 544/250
(58) Field of Classification Search ................ 544/250; 514/267

See application file for complete search history.

(56) References Cited

U.S. PATENT DOCUMENTS 6,482,948 B1    11/2002   Yamada et al.

FOREIGN PATENT DOCUMENTS

WO         WO 0059912           10/2000

*Primary Examiner*—Venkataraman Balasubramanian
(74) *Attorney, Agent, or Firm*—Millen, White, Zelano, Branigan, P.C.

(57) ABSTRACT

The invention relates to compounds of the formula (I) in which $R^1$, $E^2$ and X are as defined above.

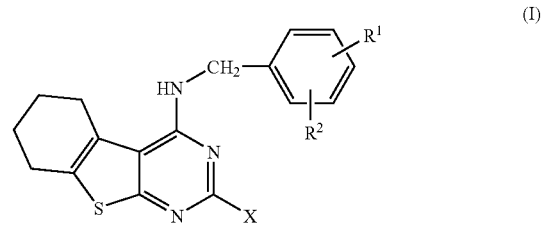

(I)

16 Claims, No Drawings

SULFAMIDOTHIENOPYRIMIDINES

The invention relates to compounds of the formula I

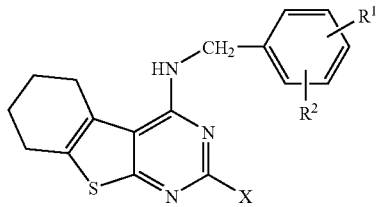

in which

R¹ and R² are each, independently of one another, H, OA¹, OCOA¹, OH or Hal, where R¹ and R² together are alternatively alkylene having 3–5 carbon atoms, —O—CH$_2$—CH$_2$—, —CH$_2$—O—CH$_2$—, —O—CH$_2$—O— or —O—CH$_2$—CH$_2$—O—, X is —CH$_2$SO$_2$NR$^3$R$^4$, R³ and R⁴, independently of one another, are H, a heteroaromatic radical, alkyl or alkenyl having 1–10 carbon atoms, each of which is unsubstituted or terminally substituted by —NH$_2$, NHA¹ or —NA¹A² and in which one or two CH$_2$ groups may be replaced by —CH═CH— groups, —O—, —NH— or —NA¹—, where R³ and R⁴ together are alternatively cycloalkyl or cycloalkylene having 3–7 carbon atoms, each of which is unsubstituted or monosubstituted or polysubstituted by Hal, —NH$_2$, —NHA, —NA¹A², —NHCOA¹, NHCOOA¹, —COOH, —COOA¹, —CONH$_2$, —CONHA¹, or —CONA¹A² and in which one or two —CH$_2$— groups may be replaced by —O—, —NH—, —NA¹—, —NCOA¹— or —NCOOA¹, A¹ and A² are each, independently of one another, alkyl or alkenyl having from 1 to 10 carbon atoms, each of which may be substituted by from 1 to 5 F and/or Cl atoms, where A¹ and A² together are alternatively cycloalkyl or cycloalkylene having 3–7 carbon atoms, in which one CH$_2$ group may be replaced by —O—, —NH—, —NA¹—, —NCOA¹— or —NCOOA¹—, and Hal is F, Cl, Br or I, and salts and/or solvates thereof.

Pyrimidine derivatives are known, for example, from DE 19819023, EP 201 188 or WO 93/06104.

The invention had the object of finding novel compounds having valuable properties, in particular those which can be used for the preparation of medicaments.

It has been found that the compounds of the formula I and salts thereof have very valuable pharmacological properties and are well tolerated.

In particular, they exhibit specific inhibition of cGMP phosphodiesterase (PDE V).

Compared with the compounds from the prior art, the compounds according to the invention have more favourable physical/chemical properties. Thus, they have better solubility and are, for example, absorbed better on oral administration.

Quinazolines having a cGMP phosphodiesterase-inhibiting activity are described, for example, in J. Med. Chem. 36, 3765 (1993) and ibid. 37, 2106 (1994).

The biological activity of the compounds of the formula I can be determined by methods as described, for example, in WO 93/06104.

The affinity of the compounds according to the invention for cGMP and cAMP phosphodiesterase is determined by measuring their IC$_{50}$ values (concentration of the inhibitor needed to achieve 50% inhibition of the enzyme activity).

The determinations can be carried out using enzymes isolated by known methods (for example W. J. Thompson et al., Biochem. 1971, 10, 311). The experiments can be carried out using a modified batch method of W. J. Thompson and M. M. Appleman (Biochem. 1979, 18, 5228).

The compounds are therefore suitable for the treatment of diseases of the cardiovascular system, in particular cardiac insufficiency, and for the treatment and/or therapy of potency disorders (erectile dysfunction).

The use of substituted pyrazolopyrimidinones for the treatment of impotence is described, for example, in WO 94/28902.

The use of other PDE V inhibitors is described, for example, in WO 94/28902.

The compounds are effective as inhibitors of phenylephrine-induced contractions in corpus cavernosum preparations of rabbits. This biological action can be demonstrated, for example, by the method described by F. Holmquist et al. in J. Urol., 150, 1310–1315 (1993).

The inhibition of the contraction demonstrates the effectiveness of the compounds according to the invention for the therapy and/or treatment of potency disorders.

Pharmaceutical formulations consisting of other phosphodiesterase V (PDE V) inhibitors together with a second active ingredient are described in WO 00/15639.

Other combinations are disclosed in WO 00/15228.

Pharmaceutical formulations consisting of other phosphodiesterase V (PDE V) inhibitors together with a prostaglandin or prostaglandin derivative are described in WO 00/15639 and WO 00/15228.

The use of (other) phosphodiesterase IV or V inhibitors in combination with a prostaglandin or prostaglandin derivative for the local treatment of erectile dysfunction is described in WO 99/21558.

R. T. Schermuly et al. in the *American Journal of Respiratory and Critical Care Medicine,* 160, 1500–6 (1999), describe the therapeutic potential of prostaglandin I$_2$ (PGI$_2$) in aerosol form with systemic PDE inhibitors, preferably dual-selective PDE III/IV inhibitors, in low doses for acute and chronic pulmonary hypertension.

In *Pneumologie* (54, Suppl. 1, S42, 2000), R. Schermuly et al. describe the influence of PDE-V inhibition on prostacyclin-induced vasorelaxation in experimental pulmonary hypertonia.

Pharmaceutical formulations consisting of other phosphodiesterase V (PDE V) inhibitors together with calcium antagonists (=calcium channel blockers) are described in WO 00/15639.

Combinations of PDE V inhibitors with endothelin receptor antagonists are described, for example, in WO 99/64004.

Pharmaceutical formulations consisting of other phosphodiesterase V (PDE V) inhibitors together with a nitrate are described in WO 00/15228. The known contraindication of administration of nitrates at the same time as taking of PDE V inhibitors in the indication of erectile dysfunction is described, for example, in WO 00/10542. At the same time, however, it is disclosed that nitrates can be administered as antianginal agents although phosphodiesterase V inhibitors are used at the same time for treatment of erectile dysfunction.

This specification furthermore describes pharmaceutical preparations which comprise both a nitrate and a phosphodiesterase inhibitor for use in the therapy of erectile dysfunction and/or in the therapy of cardiovascular diseases at the same time as the presence of the respective other indication.

The compounds according to the invention are furthermore suitable for the treatment of angina, high blood pressure, pulmonary hypertension, congestive heart failure, cardiac infarction, chronic obstructive pulmonary disease (COPD), cor pulmonale, dextrocardiac insufficiency, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis, for the treatment of female sexual disorders, inflammation, osteoporosis, furthermore for the treatment of malign hypertonia, phaeochromacytoma (catecholamine-producing tumour of the adrenal cortex), in peripheral vascular (occlusion) diseases, vascular diseases, thrombocytopenia, ulcus pepticum (benign intestinal ulcer), peristaltic motion disorders, percutaneous transluminal coronary angioplasty, carotid angioplasty, postoperative stenosis of the coronary bypass, premonitory pains and benign prostate hyperplasia.

The invention thus relates to the compounds of the formula I and thereof salts and solvates thereof, in particular physiologicaly acceptable salts and/or solvates thereof.

The compounds of the formula I can be employed as medicament active ingredients in human and veterinary medicine. They can furthermore be employed as intermediates for the preparation of further medicament active ingredients.

Above and below, the radicals $R^1$, $R^2$, $R^3$, $R^4$, $A^1$, $A^2$, X and L are as defined in the formulae I, II and III, unless expressly stated otherwise.

$R^1$ and $R^2$ are preferably, independently of one another, H, $OA^1$ or Hal, in particular alkoxy having from 1 to 9 carbon atoms, Cl, Br or F.

$R^3$ and $R^4$ are, independently of one another, preferably H, a heteroaromatic radical or alkyl having from 1 to 10 carbon atoms which is terminally substituted by $-NH_2$, $-NHA^1$ or $-NA^1A^2$, in which $A^1$ is as defined above. Furthermore, $R^3$ and $R^4$ together are preferably alternatively cycloalkyl or cycloalkylene having 3–7 carbon atoms, each of which is unsubstituted or monosubstituted or polysubstituted by $-NH_2$, $-NHA$, $-NA^1A^2$, $-NHCOA^1$, $NHCOOA^1$, $-COOH$, $-COOA^1$, $-CONH_2$, $-CONHA^1$, or $-CONA^1A^2$ and in which one or two $-CH_2-$ groups may be replaced by $-O-$, $-NH-$, $-NA^1-$, $-NCOA^1-$ or $-NCOOA^1$. In particular, $R^3$ and $R^4$, independently of one another, are H, alkyl having from 1 to 8 carbon atoms which is terminally substituted by $-NH_2$, $-NHCH_3$ or $-N(CH_3)_2$, or one of the following groups:

in which n is 0, 1, 2, 3, 4, 5, 6, 7, 8, 9 or 10, preferably 0 or 2.

In the formulae above or below, alkyl is preferably unbranched and has 1, 2, 3, 4, 5, 6, 7 or 8 carbon atoms and is particularly preferably methyl, ethyl or propyl, furthermore isopropyl, butyl, isobutyl, sec-butyl or tert-butyl, but also n-pentyl, neopentyl, isopentyl or hexyl.

$A^1$ and $A^2$ are each, independently of one another, preferably alkyl having from 1 to 7 carbon atoms, where $A^1$ and $A^2$ together are alternatively cycloalkylene having 3–7 carbon atoms, in which one $CH_2$ group may be replaced by $-O-$, $-NH-$, $-NA^1-$, $-NCOA^1-$ or $-NCOOA^1-$. In particular, $A^1$ and $A^2$ are methyl or ethyl.

Hal is preferably F, Cl or Br, but also I, but in particular Cl.

The radicals $R^1$ and $R^2$ may be identical or different and are preferably in the 3- and 4-position of the phenyl ring. They are, for example, each, independently of one another, H, OH, Oalkyl, F, Cl, Br or I or together are alkylene, such as, for example, propylene, butylene or pentylene, furthermore ethyleneoxy, methylenedioxy or ethylenedioxy. They are alternatively preferably each alkoxy, such as, for example, methoxy, ethoxy or propoxy, furthermore hydroxyl.

The term "heteroaromatic radical" is preferably pyridyl, pyrazolyl, imidazolyl, oxazolyl, isoxazolyl, thiazolyl, triazolyl, quinolinyl, isoquinolinyl, acridinyl, pyridazyl, pyrimidyl, pyrazinyl, phenazinyl, 9H-purinyl, pteridyl, in particular 2,3 or 4-pyridyl, pyridazyl, pyrimidyl, pyrazinyl, pyrazolyl and imidazolyl.

Throughout the invention, all radicals which occur more than once may be identical or different, i.e. are independent of one another.

Accordingly, the invention relates, in particular, to the use of the compounds of the formula I in which at least one of the said radicals has one of the preferred meanings indicated above.

Particular preferred compounds of the formula I are the compounds I1 to I9:

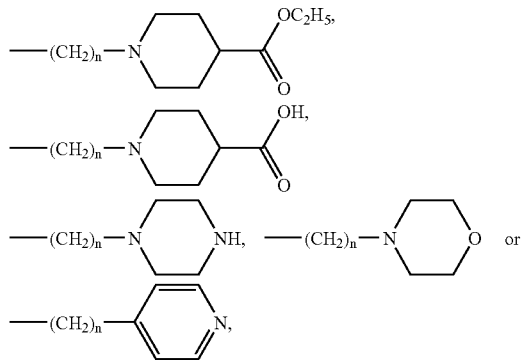

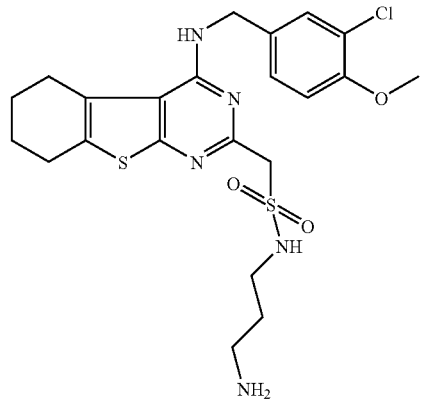

I1

-continued
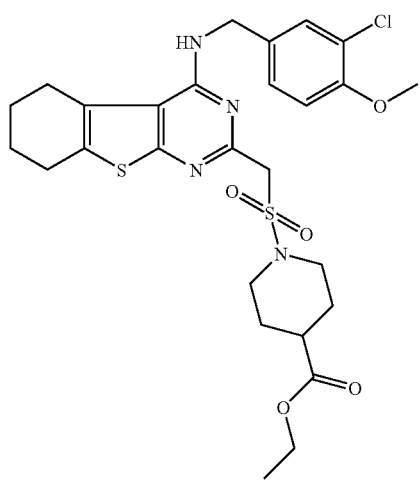
I2
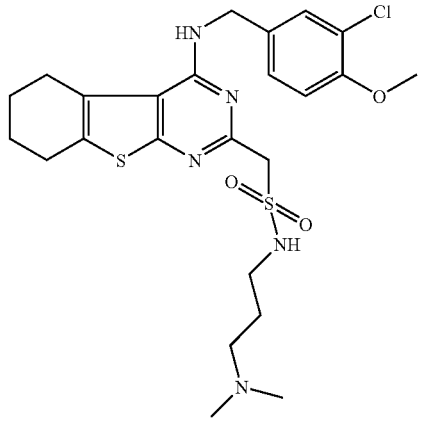
I5
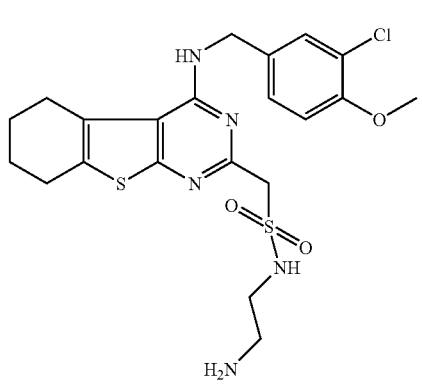
I6
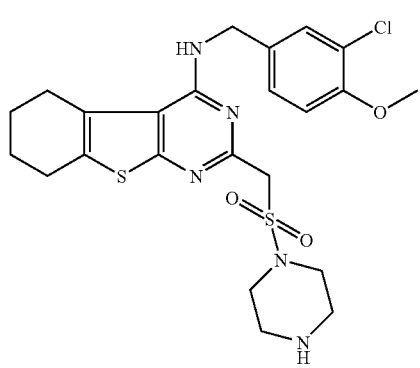
I3
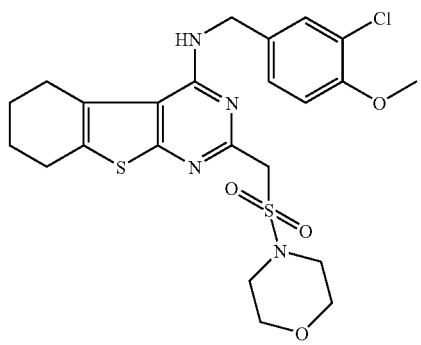
I7
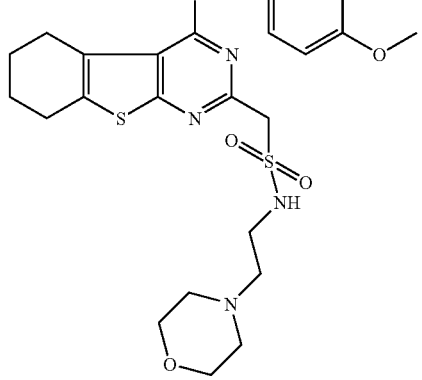
I8
I4

-continued

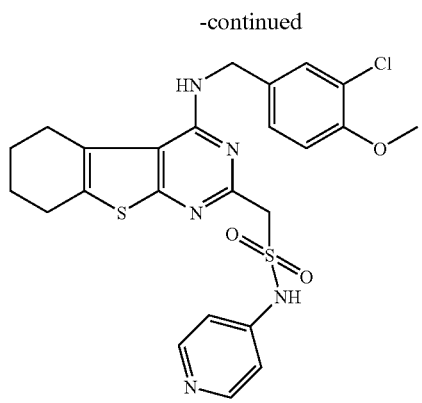

I9 and salts and solvates thereof. The ethanolammonium salt of compound I3 is particularly preferred.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

In the compounds of the formulae II and III, $R^1$, $R^2$ and X have the meanings indicated, in particular the preferred meanings indicated.

If L is a reactive esterified OH group, this is preferably alkylsulfonyloxy having 1–6 carbon atoms (preferably methylsulfonyloxy) or arylsulfonyloxy having 6–10 carbon atoms (preferably phenyl- or p-tolylsulfonyloxy, furthermore also 2-naphthalenesulfonyloxy).

The compounds of the formula I can preferably be obtained by a process in which compounds of the formula II

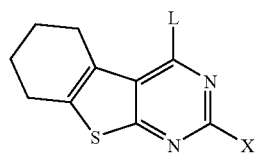

II in which
X is as defined above,
and L is Cl, Br, OH, $SCH_3$ or a reactive esterified OH group, are reacted with compounds of the formula III

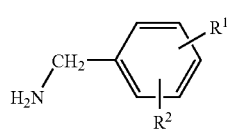

III in which
$R^1$ and $R^2$ are as defined above, or
a compound of the formula IV

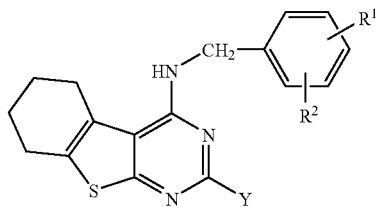

IV in which
Y is $—CH_2SO_2Q$,
Q is Cl, Br, OH or a reactive esterified OH group, and
$R^1$ and $R^2$ are as defined in claim 1,
is reacted with a compound of the formula V

HNR³R⁴   V in which
$R^3$ and $R^4$ are as defined in claim 1, or
and/or in that a compound of the formula I is converted into one of its salts.

If desired, the starting materials can also be formed in situ by not isolating them from the reaction mixture, but instead immediately converting them further into the compounds of the formula I.

On the other hand, it is possible to carry out the reaction stepwise.

The starting compounds of the formula II and III are generally known. If they are not known, they can be prepared by methods known per se. Compounds of the formula II can be obtained, for example, from the corresponding hydroxypyrimidines, which are built up from thiophene derivatives and CN-substituted alkylenecarboxylic acid esters (Eur. J. Med. Chem. 23, 453 (1988)), by reaction with $POCl_3$.

The hydroxypyrimidines are prepare by the cyclisation of 2-aminothiophene-3-carboxylic acid derivatives using aldehydes or nitriles which is usual for the preparation of pyrimidine derivatives (for example Houben Weyl E9b/2).

In detail, the reaction of the compounds of the formula II with the compounds of the formula III is carried out in the presence or absence of an inert solvent at temperatures between about −20 and about 150°, preferably between 20 and 100°.

The addition of an acid-binding agent, for example an alkali or alkaline earth metal hydroxide, carbonate or bicarbonate or another salt of a weak acid of the alkali or alkaline earth metals, preferably of potassium, sodium or calcium, or the addition of an organic base, such as triethylamine, dimethylamine, pyridine or quinoline or of an excess of the amine component, may be favourable.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone or dimethylformamide (DMF); nitriles, such as acetonitrile; sulfoxides, such as dimethyl sulfoxide (DMSO); nitro compounds, such as nitromethane or nitrobenzene; esters, such as ethyl acetate, or mixtures of the said solvents.

It is furthermore possible to convert a radical $R^1$ or $R^2$ in a compound of the formula I into another radical $R^1$ or $R^2$, for example by hydrolysing an ester to give an OH group.

Ester groups can be saponified, for example, using NaOH or KOH in water, water/THF or water/dioxane at temperatures between 0 and 100°. Ethers can be obtained by alkylation of the resultant hydroxyl groups under standard conditions.

An acid of the formula I can be converted into the associated acid-addition salt using a base, for example by reaction of equivalent amounts of the acid and the base in an inert solvent, such as ethanol, followed by evaporation. Suitable bases for this reaction are, in particular, those which give physiologically acceptable salts.

Thus, the acid of the formula I can be converted into the corresponding metal salt, in particular alkali metal or alkaline earth metal salt, or into the corresponding ammonium salt using a base (for example sodium hydroxide, potassium hydroxide, sodium carbonate or potassium carbonate). Also suitable for this reaction are, in particular, organic bases which give physiologically acceptable salts, such as, for example, ethanolamine.

On the other hand, a base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable acids. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane-or ethanesulfonic acid, ethanedisulfonic acid, 2-hydroxyethanesulfonic acid, benzenesulfonic acid, p-toluenesulfonic acid, naphthalenemono-and-disulfonic acids, or laurylsulfuric acid. Salts with physiologically unacceptable acids, for example picrates, can be used for the isolation and/or purification of the compounds of the formula I.

The invention furthermore relates to pharmaceutical preparations comprising at least one compound of the formula I and/or one of its physiologically acceptable salts and/or solvates for the treatment of angina, high blood pressure, pulmonary hypertension, congestive heart failure, atherosclerosis, conditions of reduced patency of heart vessels, peripheral vascular diseases, strokes, bronchitis, allergic asthma, chronic asthma, allergic rhinitis, glaucoma, irritable bowel syndrome, tumours, renal insufficiency, liver cirrhosis and for the treatment of female impotence.

These preparations can be used as medicaments in human or veterinary medicine. Suitable excipients are organic or inorganic substances which are suitable for enteral (for example oral), parenteral or topical administration and do no react with the novel compounds, for example water, vegetable oils, benzyl alcohols, alkylene glycols, polyethylene glycols, glycerol triacetate, gelatine, carbohydrates, such as lactose or starch, magnesium stearates, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, colorants and flavours and/or a plurality of further active ingredients, for example one or more vitamins.

The compounds of the formula I and physiologically acceptable salts thereof can be employed in the treatment and prophylaxis of diseases which are caused by an excessively low cGMP (cycloguanosine monophosphate) level and/or can be influenced by an increase in the cGMP level. The increased cGMP level causes inhibition or prevention of inflammation and causes relaxation of muscles. In particular, the compounds according to the invention can be employed in the treatment of angina, high blood pressure, pulmonary hypertension, congestive heart failure, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis and for the treatment of female impotence.

The invention relates to the use of the compounds of the formula I and physiologically acceptable salts and/or solvates thereof for the preparation of a medicament for the treatment and prophylaxis of potency disorders, such as, for example, erectile dysfunction, for the treatment and prophylaxis of angina, high blood pressure, pulmonary hypertension, congestive heart failure, cardiac infarction, chronic obstructive pulmonary disease (COPD), cor pulmonale, dextrocardiac insufficiency, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis, for the treatment of female sexual disorders, inflammation, osteoporosis, for the treatment of malign hypertonia, phaeochromacytoma, peripheral vascular (occlusion) diseases, vascular diseases, thrombocytopenia, ulcus pepticum, peristaltic motion disorders, percutaneous transluminal coronary angioplasty, carotid angioplasty, postoperative stenosis of the coronary bypass, premonitory pains and benign prostate hyperplasia.

In general, the substances are preferably administered in doses of between about 1 and 500 mg, in particular between 5 and 100 mg per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or its physiologically tolerated salts and solvates, and at least one further medicament active ingredient.

The invention also relates to a set (kit) consisting of separate packs of
(a) an effective amount of a compound of the formula I and/or its physiologically tolerated salts and solvates, and
(b) an effective amount of a further medicament active ingredient.

The set comprises suitable containers, such as boxes, individual bottles, cartons, bags or ampoules. The set may comprise, for example, separate ampoules each containing an effective amount of a compound of the formula I and/or its physiologically tolerated salts and solvates, and an effective amount of a further medicament active ingredient in dissolved or lyophilised form.

The invention furthermore relates to the use of compounds of the formula I and/or physiologically tolerated salts and solvents thereof for the preparation of a medicament for the treatment of diseases of the cardiovascular system, for the treatment and prophylaxis of potency disorders, such as, for example, erectile dysfunction, for the treatment and prophylaxis of angina, high blood pressure, pulmonary hypertension, congestive heart failure, cardiac infarction, chronic obstructive pulmonary disease (COPD), cor pulmonale, dextrocardiac insufficiency, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis, for the treatment of female sexual disorders, inflammation, osteoporosis, furthermore for the treatment of malign hypertonia, phaeochromacytoma (catecholamine-producing tumour of the pituitary cortex), in peripheral vascular (occlusion) diseases, vascular diseases, thrombocytopenia, ulcus pepticum (benign intestinal ulcer), peristaltic motion disorders, percutaneous transluminal coronary angioplasty, carotid angioplasty, postoperative stenosis of the coronary bypass, premonitory pains and benign prostate hyperplasia, in combination with at least one further medicament active ingredient.

The compounds of the formula I according to the invention can be used together with other active ingredients, such as, for example, with vasodilators, α-adrenergic inhibitors, such as, for example, phentolamin, prazocin or yohimbin, mixed α,β-inhibitors, such as, for example, carvedilol, prostaglandin EI and prostacyclin, ACE (angiotensin converting enzyme) inhibitors, NEP (neutral endopeptidase) inhibitors, centrally acting dopaminergic active ingredients, such as, for example, apomorphine, vasoactive intestinal peptides, calcium channel blockers and compounds such as thiazides.

The invention therefore relates to pharmaceutical formulations comprising a prostaglandin or prostaglandin derivative and at least one compound of the formula I.

Preference is given to prostaglandins or prostaglandin derivatives selected from the group consisting of $PGE_0$, $PGA_1$, $PGB_1$, $PGF_{1\alpha}$, $PGA_2$, $PGB_2$, 19-hydroxy-$PGA_1$, 19-hydroxy-$PGB_1$, 19-hydroxy-$PGA_2$, 19-hydroxy-$PGB_2$, $PGE_3$, $PGF_{3\alpha}$, alprostadil ($PGE_1$), dinoprost ($PGF_2$), dinoprostone ($PGE_2$), epoprostenol sodium ($PGI_2$; prostacyclin sodium), gemeprost, iloprost, latanoprost, misoprostol, sulprostone, carboprost thromethamin, dinoprost thromethamin, lipoprost, metenoprost and tiaprost.

Particular preference is given to prostaglandins or prostaglandin derivatives selected from the group consisting of alprostadil ($PGE_1$), dinoprost ($PGF_2$), dinoprostone ($PGE_2$), epoprostenol sodium ($PGI_2$; prostacyclin sodium), gemeprost, iloprost, latanoprost, misoprostol, sulprostone, carboprost thromethamin, dinoprost thromethamin, lipoprost, metenoprost and tiaprost.

Particular preference is given to $PGE_1$ or prostacyclin, especially preferably prostacyclin.

The invention preferably relates to pharmaceutical formulations comprising a calcium antagonist and at least one compound of the formula I. Preference is given to calcium antagonists selected from the group consisting of selective and non-selective calcium antagonists.

Preference is given to selective calcium antagonists selected from the group consisting of dihydropyridine derivatives, phenylalkylamine derivatives, benzothiazepine derivatives and other selective calcium antagonists.

Dihydropyridine derivatives are preferably selected from the group consisting of amlodipine, felodipine, isradipine, nicardipine, nifedipine, nimodipine, nisoldipine, nitrendipine, lacidipine, nilvadipine, manidipine, barnidipine and lercanidipine.

The phenylalkylamine derivatives are preferably selected from the group consisting of verapamil and gallopamil.

The benzothiazepine derivatives are preferably diltiazem.

The other selective calcium antagonists are preferably mibefradil.

The non-selective calcium antagonists are preferably selected from the group consisting of fendiline, bepridil, lidoflazine and perhexiline.

The invention furthermore relates to pharmaceutical formulations comprising an antithrombotic and at least one compound of the formula I. The term antithrombotics also includes so-called anticoagulants and blood platelet aggregation inhibitors (thrombocyte aggregation inhibitors). Preferred antithrombotics are vitamin K antagonists, heparin compounds, thrombocyte aggregation inhibitors, enzymes, factor Xa inhibitors, factor VIIa inhibitors and other antithrombotic agents.

Preferred vitamin K antagonists are selected from the group consisting of dicoumarol, phenindione, warfarin, phenprocoumon, acenocoumarol, ethyl biscoumacetate, clorindione, diphenadione and tioclomarol.

Preferred heparin compounds are selected from the group consisting of heparin, antithrombin III, dalteparin, enoxaparin, nadroparin, parnaparin, reviparin, danaparoid, tinzaparin and sulodexide.

Preferred thrombocyte aggregation inhibitors are selected from the group consisting of ditazole, cloricromen, picotamide, clopidogrel, ticlopidine, acetylsalicylic acid, dipyridamole, calcium carbassalate, epoprostenol, indobufen, iloprost, abciximab, tirofiban, aloxiprin and intrifiban.

Preferred enzymes are selected from the group consisting of streptokinase, alteplase, anistreplase, urokinase, fibrinolysin, brinase, reteplase and saruplase.

Preferred antithrombotics are furthermore the blood platelet glycoprotein receptor (IIb/IIIa) antagonists which inhibit blood platelet aggregation. Preferred compounds are described, for example, in EP 0 623 615 B1 on page 2 or in EP 0 741 133 A2, page 2, line 2, to page 4, line 56.

Preferred factor Xa and VIIa inhibitors are, for example, the compounds of the formula I described in WO 9916751, WO 9931092, WO 9957096, WO 0012479, WO 0020416, WO 0040583 and WO 0051989.

Other preferred factor Xa inhibitors are, for example, the compounds described in the following documents:
a) in WO 97/30971, page 4, line 5, to page 13, line 19;
b) in EP 0 921 116 A1, page 2, line 1, to line 51;
c) in EP 0 540 051 B1, page 2, line 41, to page 3, line 14;
d) in EP 0 798 295 A1, page 69, line 10, to page 71, page 53;

Other preferred compounds are selected from the group consisting of defibrotide, desirudin and lepirudin.

The invention also relates to pharmaceutical formulations comprising an endothelin receptor antagonist and at least one compound of the formula I.

Preferred endothelin receptor antagonists are bosentan, tezosentan and sitaxentan (TBC-11251; J. Med. Chem., 40, No. 11, 1690–97, 1997). Preferred endothelin receptor antagonists are thus furthermore
a) BMS-193884 (EP 558258),
b) BMS-207940 (Pharmaprojects (13. 06. 97)),
c) BQ-123 (Exp. Opin. Invest. Drugs, 1997, 6, No. 5, 475–487),
d) SB-209670 (Exp. Opin. Invest. Drugs, 1997, 6, No. 5, 475–487),
e) SB-217242 (Exp. Opin. Invest. Drugs, 1997, 6, No. 5, 475–487),
f) SB-209598 (Trends in Pharmacol. Sci., 17, 177–81, 1996),
g) TAK-044 (Exp. Opin. Invest. Drugs, 1997, 6, No. 5, 475–487),
h) Bosentan (Trends in Pharmacol. Sci., 18, 408–12, 1997),
i) PD-156707 (J. Med. Chem., 40, No. 7, 1063–74, 1997),
j) L-749329 (Bioorg. Med. Chem. Lett., 7, No. 3, 275–280, 1997),
k) L-754142 (Exp. Opin. Invest. Drugs, 1997, 6, No. 5, 475–487),
l) ABT-627 (J. Med. Chem., 40, No. 20, 3217–27, 1997),
m) A-127772 (J. Med. Chem., 39, No. 5, 1039–1048, 1996),
n) A-206377 (213th American Chemical Society National Meeting, San Francisco, Calif., USA, Apr. 13–17, 1997, Poster, MEDI 193),
o) A-182086 (J. Med. Chem., 40, No. 20, 3217–27, 1997),
p) EMD-93246 (211th American Chemical Society National Meeting, New Orleans, USA, 1996, Poster, MEDI 143),
q) EMD-122801 (Bioorg. Med. Chem. Lett., 8, No. 1, 17–22, 1998),
r) ZD-1611 (Trends in Pharmacol. Sci., 18, 408–12, 1997),
s) AC-610612 (R&D Focus Drug News (18.05.98)),
t) T-0201 (70th Annual Meeting of the Japanese Pharmacological Society, Chiba, Japan, Mar. 22–15, 1997, Lecture, O-133),
u) J-104132 (R&D Focus Drug News (15.12.97)), v)

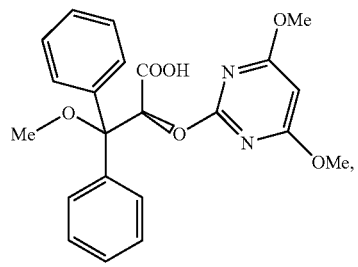

w)

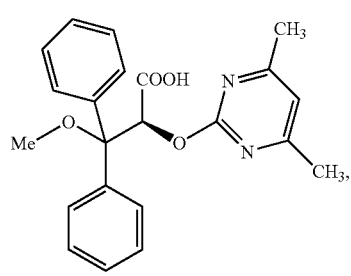

-continued x)

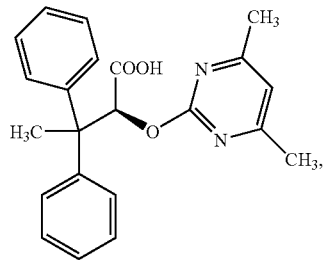

y)

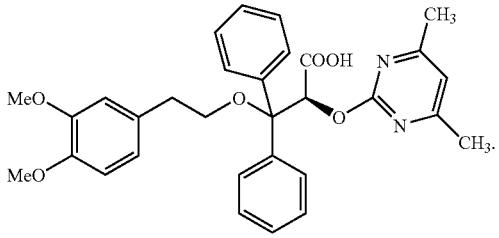

Particularly preferred endothelin receptor antagonists are, for example, the compounds of the formula I described in EP 0733626, EP 0733626, EP 0755934, EP 0757039, EP 0796250, WO 9719077, WO 9730982, WO 9730996, DE 19609597, DE 19612101, WO 9827091, WO 9827077, WO 9841515, WO 9841521, WO 9842702, WO 9842709 or WO 9905132.

The invention furthermore relates to pharmaceutical formulations comprising a vasodilator, such as, for example, a nitrate, and at least one compound of the formula I.

The invention preferably relates to pharmaceutical formulations comprising at least one compound of the formula I and a vasodilator, such as, for example, (a) an organic nitrate, for example nitroglycerin, isosorbide mononitrate, isosorbide dinitrate, pentaerythrityl tetra-, tri-, di-, tri-or mononitrate, propatyl nitrate, trol nitrate, nicroandil, mannitol hexanitrate, inositol hexanitrate, N-[3-nitratopivaloyl]-L-cycsteine ethyl ester, (b) an organic nitrite, for example isoamyl nitrite, (c) a thionitrite, (d) a thionitrate, (e) an S-nitrosothiol, such as, for example, S-nitroso-N-acetyl-D, L-penicillamine, (f) nitrosoproteins, (g) substituted furoxanes, such as, for example, 1,2,5-oxadiazole 2-oxides or furazane N-oxides, (h) substituted sydnonimines, such as, for example, molsidomine or mesocarb, (i) complex nitrosyl compounds, such as, for example, iron nitrosyl compounds, preferably sodium nitroprusside, or (j) nitrogen oxide NO, which is inhaled.

Preferred vasodilators are nitrates selected from the group consisting of pentaerythrityl tetra-, tri-, di-and mononitrate, isosorbide mononitrate, isosorbide dinitrate and glycerol trinitrate.

Particular preference is given to nitrates selected from the group consisting of pentaerythrityl tetranitrate, isosorbide mononitrate, isosorbide dinitrate, glycerol trinitrate, very particularly preferably pentaerythrityl tetranitrate.

The invention furthermore relates to the use of a pharmaceutical formulation comprising at least one compound of the formula I and at least one antithrombotic for the preparation of a medicament for the treatment of pulmonary hypertension, congestive heart failure (CHF), chronic obstructive pulmonary disease (COPD), cor pulmonale and/or dextrocardiac insufficiency.

α-adrenergic inhibitors inhibit the vasoconstriction in the corpus cavernosum. Since PDE V inhibitors increase vasodilation of the same tissue of the smooth muscles, potency disorders (erectile dysfunction) can preferably also be treated using pharmaceutical formulations comprising at least one compound of the formula I and at least one α-adrenergic inhibitor, such as, for example, phentolamin or prazocin, or at least one centrally acting dopaminergic active ingredient, such as, for example, apomorphine.

The invention therefore furthermore relates to the use of a pharmaceutical formulation comprising at least one compound of the formula I and at least one α-adrenergic inhibitor, such as, for example, phentolamin or prazocin, or at least one centrally acting dopaminergic active ingredient, such as, for example, apomorphine, for the preparation of a medicament for the treatment of potency disorders.

The invention furthermore relates to the use of a pharmaceutical formulation comprising at least one compound of the formula I and a calcium antagonist for the preparation of a medicament for the treatment of pulmonary hypertension, congestive heart failure (CHF), chronic obstructive pulmonary disease (COPD), cor pulmonale and/or dextrocardiac insufficiency.

The invention furthermore relates to the use of a pharmaceutical formulation comprising at least one compound of the formula I and at least one nitrate for the preparation of a medicament for the treatment of pulmonary hypertension, congestive heart failure (CHF), chronic obstructive pulmonary disease (COPD), cor pulmonale and/or dextrocardiac insufficiency.

The invention furthermore relates to the use of a pharmaceutical formulation comprising at least one compound of the formula I and at least one endothelin receptor antagonist for the preparation of a medicament for the treatment of pulmonary hypertension, congestive heart failure (CHF), chronic obstructive pulmonary disease (COPD), cor pulmonale and/or dextrocardiac insufficiency.

The invention furthermore relates to the use of a pharmaceutical formulation comprising at least one compound of the formula I and at least one prostaglandin or a prostaglandin derivative for the preparation of a medicament for the treatment of pulmonary hypertension, congestive heart failure (CHF), chronic obstructive pulmonary disease (COPD), cor pulmonale and/or dextrocardiac insufficiency.

Accordingly, the present application particularly preferably relates to medicaments comprising at least one compound of the formula I and/or its physiologically acceptable salts and solvates and at least one further medicament active ingredient selected from the following group a) to k):
  a) prostaglandin or prostaglandin derivative,
  b) calcium antagonist,
  c) antithrombotic,
  d) endothelin receptor antagonist,
  e) nitrate,
  f) α-adrenergic inhibitor,
  g) centrally acting dopaminergic active ingredient,
  h) ACE inhibitor,
  i) NEP inhibitor,
  j) mixed α,β-inhibitor,
  k) vasoactive intestinal peptide.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

Mass spectrometry (MS): EI (electron impact ionisation) $M^+$ FAB (fast atom bombardment) $(M+H)^+$ The invention relates, in particular, to the compounds of the formula I given in the following examples and physiologically acceptable salts and/or solvates thereof and to the use thereof for the preparation of a medicament for the treatment of angina, high blood pressure, pulmonary hypertension, congestive heart failure, atherosclerosis, conditions of reduced patency of the heart vessels, peripheral vascular diseases, strokes, bronchitis, allergic asthma, chronic asthma, allergic rhinitis, glaucoma, irritable bowel syndrome, tumours, renal insufficiency, liver cirrhosis and for the treatment of female impotence.

EXAMPLE 1

Step A:

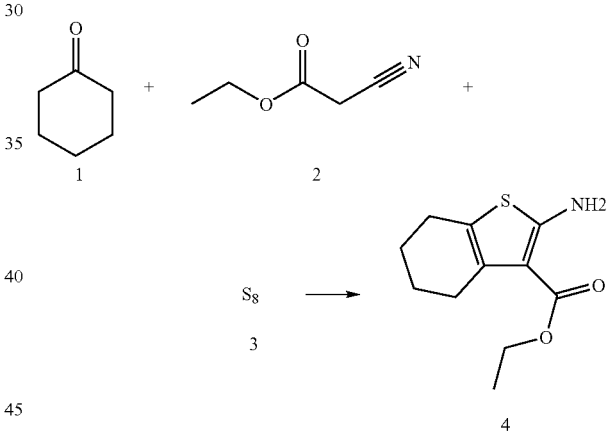

99.0 g of sulfur were introduced with stirring into a mixture of 300 ml of 2, 290 ml of cyclohexanone and 670 ml of ethanol. 275 ml of diethylamine were subsequently added dropwise at from about 50° C. to 65° C., and the resultant precipitate was filtered off and recrystallised from ethanol, giving 4.

Step B:

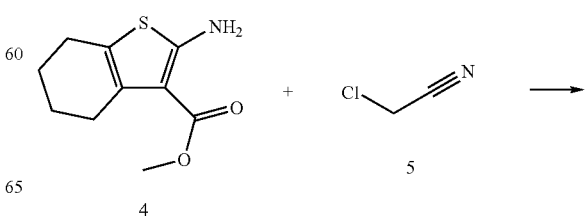

-continued

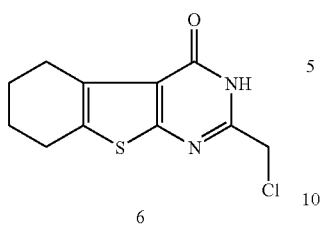

6

About 500 g of HCl were passed into a solution of 350,0 g of 4 and 132 ml of chloroacetonitrile in 2 l of dioxane over the course of 3 hours with stirring, during which the temperature is held at 45° C. After the solvent had been removed, and the mixture had been rendered alkaline with bicarbonate solution and filtered, 6 was obtained in crystalline form.

Step C:

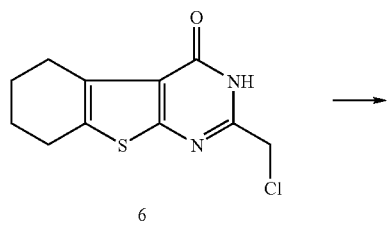

6

400.0 g of 6 were introduced at 25–30° C. into a mixture of 1.00 l of thionyl chloride with 123.116 ml of N,N-dimethylformamide. The mixture was subsequently stirred overnight at RT and subjected to conventional work-up, giving 7 in crystalline form.

Step D:

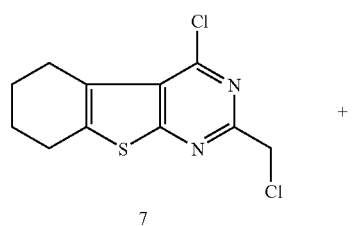

7

+

-continued

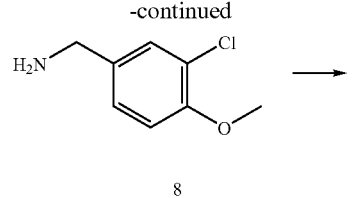

8

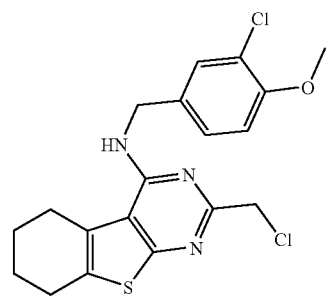

9

384.0 g of 7 were introduced into 4 l of THF, and 514.88 g of 8, dissolved in 1 l of THF, were rapidly added dropwise at 20° C. with gentle ice-water cooling. The mixture was stirred overnight and subjected to conventional work-up, giving 9 in the form of crystals (m.p. 120–121° C.)

Step E:

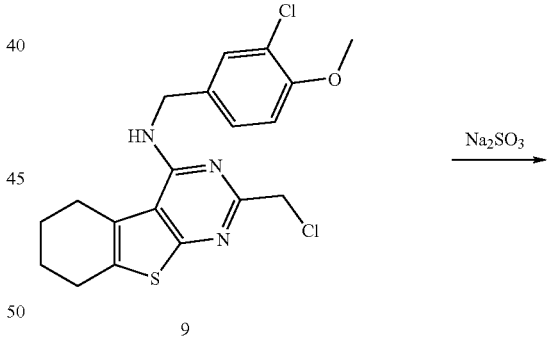

9

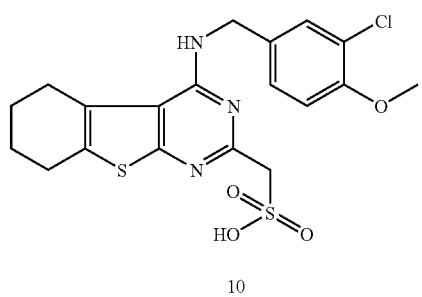

10

100 ml of a saturated solution of sodium sulfite in water were added to a solution of 15,00 g of 9 in 60 ml of dioxane. Stirring overnight and conventional work-up gave 10.

Step F:

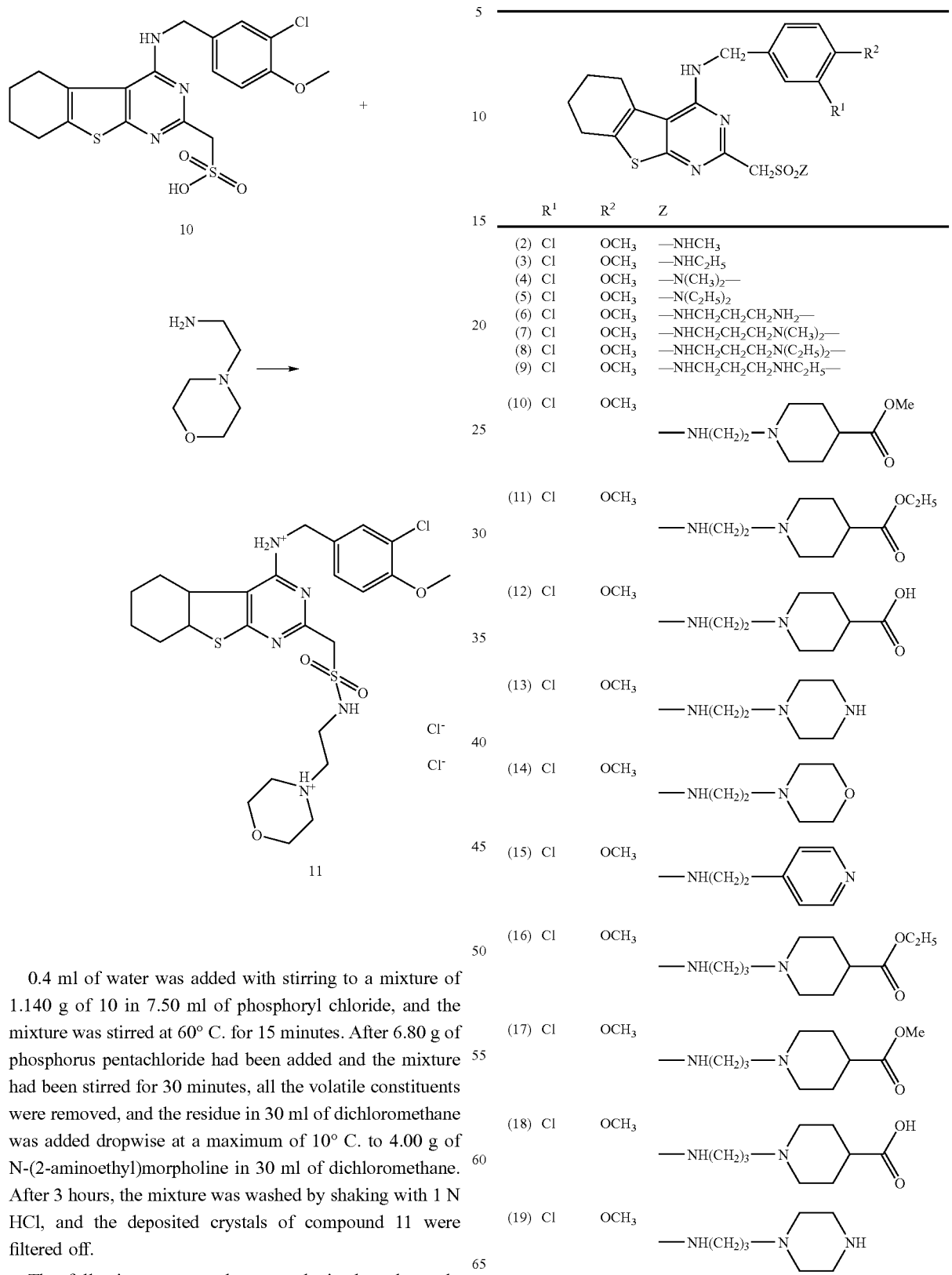

0.4 ml of water was added with stirring to a mixture of 1.140 g of 10 in 7.50 ml of phosphoryl chloride, and the mixture was stirred at 60° C. for 15 minutes. After 6.80 g of phosphorus pentachloride had been added and the mixture had been stirred for 30 minutes, all the volatile constituents were removed, and the residue in 30 ml of dichloromethane was added dropwise at a maximum of 10° C. to 4.00 g of N-(2-aminoethyl)morpholine in 30 ml of dichloromethane. After 3 hours, the mixture was washed by shaking with 1 N HCl, and the deposited crystals of compound 11 were filtered off.

The following compounds were obtained analogously using the corresponding precursors:

EXAMPLES 2–81

-continued

Common structure (col 21 and col 22): tetrahydrobenzothienopyrimidine with 4-NH-CH2-aryl(R1,R2) and 2-CH2SO2Z substituents.

| # | R¹ | R² | Z |
|---|----|----|---|
| (20) | Cl | OCH₃ | —NH(CH₂)₃-morpholino |
| (21) | Cl | OCH₃ | —NH(CH₂)₃-(4-pyridyl) |
| (22) | Cl | OCH₃ | —NHCH₃ |
| (23) | Cl | OCH₃ | —NHC₂H₅ |
| (24) | Cl | OCH₃ | —N(CH₃)₂— |
| (25) | Cl | OCH₃ | —N(C₂H₅)₂— |
| (26) | Cl | OCH₃ | —NHCH₂CH₂CH₂NH₂— |
| (27) | Cl | OCH₃ | —NHCH₂CH₂CH₂N(CH₃)₂— |
| (28) | Cl | OCH₃ | —NHCH₂CH₂CH₂N(C₂H₅)₂— |
| (29) | Cl | OCH₃ | —NHCH₂CH₂CH₂NHC₂H₅— |
| (30) | Cl | OCH₃ | —NH(CH₂)₃-(4-methoxycarbonyl-piperidin-1-yl) |
| (31) | Cl | OC₂H₅ | —NH(CH₂)₃-(4-ethoxycarbonyl-piperidin-1-yl) |
| (32) | Cl | OC₂H₅ | —NH(CH₂)₂-(4-carboxy-piperidin-1-yl) |
| (33) | Cl | OC₂H₅ | —NH(CH₂)₂-piperazin-1-yl |
| (34) | Cl | OC₂H₅ | —NH(CH₂)₂-morpholino |
| (35) | Cl | OC₂H₅ | —NH(CH₂)₂-(4-pyridyl) |
| (36) | Cl | OC₂H₅ | —NH(CH₂)₃-(4-ethoxycarbonyl-piperidin-1-yl) |
| (37) | Cl | OC₂H₅ | —NH(CH₂)₃-(4-methoxycarbonyl-piperidin-1-yl) |
| (38) | Cl | OC₂H₅ | —NH(CH₂)₃-(4-carboxy-piperidin-1-yl) |
| (39) | Cl | OC₂H₅ | —NH(CH₂)₃-piperazin-1-yl |
| (40) | Cl | OC₂H₅ | —NH(CH₂)₃-morpholino |
| (41) | Cl | OC₂H₅ | —NH(CH₂)₃-(4-pyridyl) |
| (42) | OCH₃ | Cl | —NHCH₃ |
| (43) | OCH₃ | Cl | —NHC₂H₅ |
| (44) | OCH₃ | Cl | —N(CH₃)₂— |
| (45) | OCH₃ | Cl | —N(C₂H₅)₂— |
| (46) | OCH₃ | Cl | —NHCH₂CH₂CH₂NH₂— |
| (47) | OCH₃ | Cl | —NHCH₂CH₂CH₂N(CH₃)₂— |
| (48) | OCH₃ | Cl | —NHCH₂CH₂CH₂N(C₂H₅)₂— |
| (49) | OCH₃ | Cl | —NHCH₂CH₂CH₂NHC₂H₅— |
| (50) | OCH₃ | Cl | —NH(CH₂)₂-(4-methoxycarbonyl-piperidin-1-yl) |
| (51) | OCH₃ | Cl | —NH(CH₂)₂-(4-ethoxycarbonyl-piperidin-1-yl) |
| (52) | OCH₃ | Cl | —NH(CH₂)₂-(4-carboxy-piperidin-1-yl) |
| (53) | OCH₃ | Cl | —NH(CH₂)₂-piperazin-1-yl |
| (54) | OCH₃ | Cl | —NH(CH₂)₂-morpholino |
| (55) | OCH₃ | Cl | —NH(CH₂)₂-(4-pyridyl) |
| (56) | OCH₃ | Cl | —NH(CH₂)₃-(4-ethoxycarbonyl-piperidin-1-yl) |
| (57) | OCH₃ | Cl | —NH(CH₂)₃-(4-methoxycarbonyl-piperidin-1-yl) |

-continued

Structure: 4-(benzylamino)-tetrahydrobenzothieno[2,3-d]pyrimidine with 4-R², 3-R¹ substitution on phenyl, and CH₂SO₂Z at 2-position of pyrimidine.

| | R¹ | R² | Z |
|---|---|---|---|
| (58) | OCH₃ | Cl | —NH(CH₂)₃—N(piperidine-4-COOH) |
| (59) | OCH₃ | Cl | —NH(CH₂)₃—N(piperazine-NH) |
| (60) | OCH₃ | Cl | —NH(CH₂)₃—N(morpholine) |
| (61) | OCH₃ | Cl | —NH(CH₂)₃—(4-pyridyl) |
| (62) | OCH₃ | Cl | —NHCH₃ |
| (63) | OCH₃ | Cl | —NHC₂H₅ |
| (64) | OCH₃ | Cl | —N(CH₃)₂— |
| (65) | OCH₃ | Cl | —N(C₂H₅)₂ |
| (66) | OCH₃ | Cl | —NHCH₂CH₂CH₂NH₂— |
| (67) | OCH₃ | Cl | —NHCH₂CH₂CH₂N(CH₃)₂— |
| (68) | OCH₃ | Cl | —NHCH₂CH₂CH₂N(C₂H₅)₂— |
| (69) | OCH₃ | Cl | —NHCH₂CH₂CH₂NHC₂H₅— |
| (70) | OCH₃ | Cl | —NH(CH₂)₂—N(piperidine-4-COOMe) |
| (71) | OC₂H₅ | Cl | —NH(CH₂)₂—N(piperidine-4-COOC₂H₅) |
| (72) | OC₂H₅ | Cl | —NH(CH₂)₂—N(piperidine-4-COOH) |
| (73) | OC₂H₅ | Cl | —NH(CH₂)₂—N(piperazine-NH) |
| (74) | OC₂H₅ | Cl | —NH(CH₂)₂—N(morpholine) |
| (75) | OC₂H₅ | Cl | —NH(CH₂)₂—(4-pyridyl) |
| (76) | OC₂H₅ | Cl | —NH(CH₂)₃—N(piperidine-4-COOC₂H₅) |
| (77) | OC₂H₅ | Cl | —NH(CH₂)₃—N(piperidine-4-COOMe) |
| (78) | OC₂H₅ | Cl | —NH(CH₂)₃—N(piperidine-4-COOH) |
| (79) | OC₂H₅ | Cl | —NH(CH₂)₃—N(piperazine-NH) |
| (80) | OC₂H₅ | Cl | —NH(CH₂)₃—N(morpholine) |
| (81) | OC₂H₅ | Cl | —NH(CH₂)₃—(4-pyridyl) |

EXAMPLES 82–161

Structure: 4-(benzylamino)-tetrahydrobenzothieno[2,3-d]pyrimidine with 3-R¹, 5-R² substitution on phenyl, and CH₂SO₂Z at 2-position.

| | R¹ | R² | Z |
|---|---|---|---|
| (82) | Cl | OCH₃ | —NHCH₃ |
| (83) | Cl | OCH₃ | —NHC₂H₅ |
| (84) | Cl | OCH₃ | —N(CH₃)₂— |
| (85) | Cl | OCH₃ | —N(C₂H₅)₂ |
| (86) | Cl | OCH₃ | —NHCH₂CH₂CH₂NH₂ |
| (87) | Cl | OCH₃ | —NHCH₂CH₂CH₂N(CH₃)₂— |
| (88) | Cl | OCH₃ | —NHCH₂CH₂CH₂N(C₂H₅)₂— |
| (89) | Cl | OCH₃ | —NHCH₂CH₂CH₂NHC₂H₅— |
| (90) | Cl | OCH₃ | —NH(CH₂)₂—N(piperidine-4-COOMe) |

-continued

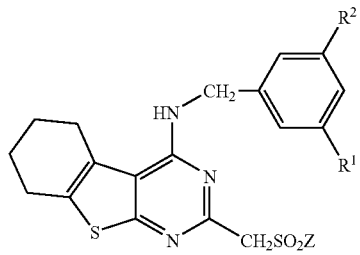

| | R¹ | R² | Z |
|---|---|---|---|
| (91) | Cl | OCH₃ | —NH(CH₂)₂-N(piperidine-4-CO₂C₂H₅) |
| (92) | Cl | OCH₃ | —NH(CH₂)₂-N(piperidine-4-COOH) |
| (93) | Cl | OCH₃ | —NH(CH₂)₂-N(piperazine-NH) |
| (94) | Cl | OCH₃ | —NH(CH₂)₂-N(morpholine) |
| (95) | Cl | OCH₃ | —NH(CH₂)₂-(4-pyridyl) |
| (96) | Cl | OCH₃ | —NH(CH₂)₃-N(piperidine-4-CO₂C₂H₅) |
| (97) | Cl | OCH₃ | —NH(CH₂)₃-N(piperidine-4-CO₂Me) |
| (98) | Cl | OCH₃ | —NH(CH₂)₃-N(piperidine-4-COOH) |
| (99) | Cl | OCH₃ | —NH(CH₂)₃-N(piperazine-NH) |
| (100) | Cl | OCH₃ | —NH(CH₂)₃-N(morpholine) |
| (101) | Cl | OCH₃ | —NH(CH₂)₃-(4-pyridyl) |
| (102) | Cl | OCH₃ | —NHCH₃ |
| (103) | Cl | OCH₃ | —NHC₂H₅ |
| (104) | Cl | OCH₃ | —N(CH₃)₂— |
| (105) | Cl | OCH₃ | —N(C₂H₅)₂ |
| (106) | Cl | OCH₃ | —NHCH₂CH₂NH₂— |
| (107) | Cl | OCH₃ | —NHCH₂CH₂N(CH₃)₂— |

-continued

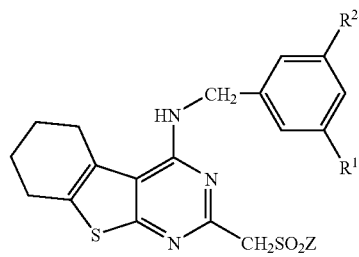

| | R¹ | R² | Z |
|---|---|---|---|
| (108) | Cl | OCH₃ | —NHCH₂CH₂CH₂N(C₂H₅)₂— |
| (109) | Cl | OCH₃ | —NHCH₂CH₂NHC₂H₅— |
| (110) | Cl | OCH₃ | —NH(CH₂)₂-N(piperidine-4-CO₂Me) |
| (111) | Cl | OC₂H₅ | —NH(CH₂)₂-N(piperidine-4-CO₂C₂H₅) |
| (112) | Cl | OC₂H₅ | —NH(CH₂)₂-N(piperidine-4-COOH) |
| (113) | Cl | OC₂H₅ | —NH(CH₂)₂-N(piperazine-NH) |
| (114) | Cl | OC₂H₅ | —NH(CH₂)₂-N(morpholine) |
| (115) | Cl | OC₂H₅ | —NH(CH₂)₂-(4-pyridyl) |
| (116) | Cl | OC₂H₅ | —NH(CH₂)₃-N(piperidine-4-CO₂C₂H₅) |
| (117) | Cl | OC₂H₅ | —NH(CH₂)₃-N(piperidine-4-CO₂Me) |
| (118) | Cl | OC₂H₅ | —NH(CH₂)₃-N(piperidine-4-COOH) |
| (119) | Cl | OC₂H₅ | —NH(CH₂)₃-N(piperazine-NH) |
| (120) | Cl | OC₂H₅ | —NH(CH₂)₃-N(morpholine) |

-continued

Structure: 4-(benzylamino)-5,6,7,8-tetrahydro[1]benzothieno[2,3-d]pyrimidine with CH₂SO₂Z at 2-position; benzyl ring substituted with R² (para) and R¹ (meta).

| | R¹ | R² | Z |
|---|---|---|---|
| (121) | Cl | OC₂H₅ | —NH(CH₂)₃-(pyridin-4-yl) |
| (122) | OCH₃ | Cl | —NHCH₃ |
| (123) | OCH₃ | Cl | —NHC₂H₅ |
| (124) | OCH₃ | Cl | —N(CH₃)₂— |
| (125) | OCH₃ | Cl | —N(C₂H₅)₂ |
| (126) | OCH₃ | Cl | —NHCH₂CH₂CH₂NH₂— |
| (127) | OCH₃ | Cl | —NHCH₂CH₂CH₂N(CH₃)₂— |
| (128) | OCH₃ | Cl | —NHCH₂CH₂CH₂N(C₂H₅)₂— |
| (129) | OCH₃ | Cl | —NHCH₂CH₂CH₂NHC₂H₅— |
| (130) | OCH₃ | Cl | —NH(CH₂)₂-(4-methoxycarbonylpiperidin-1-yl) |
| (131) | OCH₃ | Cl | —NH(CH₂)₂-(4-ethoxycarbonylpiperidin-1-yl) |
| (132) | OCH₃ | Cl | —NH(CH₂)₂-(4-carboxypiperidin-1-yl) |
| (133) | OCH₃ | Cl | —NH(CH₂)₂-(piperazin-1-yl) |
| (134) | OCH₃ | Cl | —NH(CH₂)₂-(morpholin-4-yl) |
| (135) | OCH₃ | Cl | —NH(CH₂)₂-(pyridin-4-yl) |
| (136) | OCH₃ | Cl | —NH(CH₂)₃-(4-ethoxycarbonylpiperidin-1-yl) |
| (137) | OCH₃ | Cl | —NH(CH₂)₃-(4-methoxycarbonylpiperidin-1-yl) |
| (138) | OCH₃ | Cl | —NH(CH₂)₃-(4-carboxypiperidin-1-yl) |
| (139) | OCH₃ | Cl | —NH(CH₂)₃-(piperazin-1-yl) |
| (140) | OCH₃ | Cl | —NH(CH₂)₃-(morpholin-4-yl) |
| (141) | OCH₃ | Cl | —NH(CH₂)₃-(pyridin-4-yl) |
| (142) | OCH₃ | Cl | —NHCH₃ |
| (143) | OCH₃ | Cl | NHC₂H₅ |
| (144) | OCH₃ | Cl | —N(CH₃)₂— |
| (145) | OCH₃ | Cl | —N(C₂H₅)₂ |
| (146) | OCH₃ | Cl | —NHCH₂CH₂CH₂NH₂— |
| (147) | OCH₃ | Cl | —NHCH₂CH₂CH₂N(CH₃)₂— |
| (148) | OCH₃ | Cl | —NHCH₂CH₂CH₂N(C₂H₅)₂— |
| (149) | OCH₃ | Cl | —NHCH₂CH₂CH₂NHC₂H₅— |
| (150) | OCH₃ | Cl | —NH(CH₂)₂-(4-methoxycarbonylpiperidin-1-yl) |
| (151) | OC₂H₅ | Cl | —NH(CH₂)₂-(4-ethoxycarbonylpiperidin-1-yl) |
| (152) | OC₂H₅ | Cl | —NH(CH₂)₂-(4-carboxypiperidin-1-yl) |
| (153) | OC₂H₅ | Cl | —NH(CH₂)₂-(piperazin-1-yl) |
| (154) | OC₂H₅ | Cl | —NH(CH₂)₂-(morpholin-4-yl) |
| (155) | OC₂H₅ | Cl | —NH(CH₂)₂-(pyridin-4-yl) |
| (156) | OC₂H₅ | Cl | —NH(CH₂)₃-(4-ethoxycarbonylpiperidin-1-yl) |

-continued

| | $R^1$ | $R^2$ | Z |
|---|---|---|---|
| (157) | OC$_2$H$_5$ | Cl | —NH(CH$_2$)$_3$—N⟨piperidine-COOMe⟩ |
| (158) | OC$_2$H$_5$ | Cl | —NH(CH$_2$)$_3$—N⟨piperidine-COOH⟩ |
| (159) | OC$_2$H$_5$ | Cl | —NH(CH$_2$)$_3$—N⟨piperazine-NH⟩ |
| (160) | OC$_2$H$_5$ | Cl | —NH(CH$_2$)$_3$—N⟨morpholine⟩ |
| (161) | OC$_2$H$_5$ | Cl | —NH(CH$_2$)$_3$—⟨pyridyl⟩ |

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with pump mechanism. The solution can be sprayed into the mouth or nose. One spray shot (about 0.1 ml) corresponds to a dose of about 0.14 mg.

What is claimed is:
1. A compound of the formula I

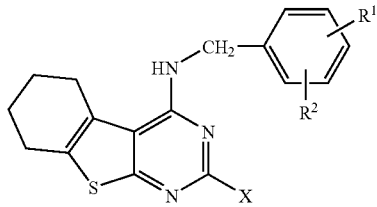

wherein
- $R^1$ and $R^2$ are each, independently of one another, H, $OA^1$, $OCOA^1$, OH or Hal, or
- $R^1$ and $R^2$ together are alkylene having 3–5 carbon atoms, —O—CH$_2$—CH$_2$—, —CH$_2$—O—CH$_2$—, —O—CH$_2$—O— or —O—CH$_2$—CH$_2$—O—,
- X is —CH$_2$SO$_2$NR$^3$R$^4$,
- $R^3$ and $R^4$, independently of one another, are H, a heteroaromatic radical, alkyl or alkenyl having 1–10 carbon atoms, each of which is unsubstituted or terminally substituted by —NH$_2$, —NHA$^1$ or —NA$^1$A$^2$ and in which one or two CH$_2$ groups may be replaced by one or more —CH=CH— groups, —O—, —NH— or —NA$^1$—, or $R^3$ and $R^4$ together are cycloalkyl or cycloalkylene having 3–7 carbon atoms, which is unsubstituted, monosubstituted or polysubstituted by —Hal, —NH$_2$, —NHA$^1$, —NA$^1$A$^2$, —NHCOA$^1$, —NHCOOA$^1$, —COOH, —COOA$^1$, —CONH$_2$, —CONHA$^1$, or —CONA$^1$A$^2$ and in which one or two —CH$_2$— groups may be replaced by —O—, —NH—, —NA$^1$—, —NCOA$^1$— or —NCOOA$^1$,
- $A^1$ and $A^2$ are each, independently of one another, alkyl or alkenyl having 1–10 carbon atoms, each of which may be substituted by 1–5 F and/or Cl atoms, or $A^1$ and $A^2$ together are cycloalkyl or cycloalkylene having 3–7 carbon atoms, in which one CH$_2$ group may be replaced by —O—, —NH—, —NA$^1$—, —NCOA$^1$— or —NCOOA$^1$—, and
- Hal is F, Cl, Br or I, or a physiologically acceptable salt thereof.

2. A compound of the formula I according to claim 1, wherein $R^1$ and $R^2$, independently of one another, are H, $OA^1$, Cl, Br or F.

3. A compound of the formula I according to claim 1, wherein $R^3$ and $R^4$, independently of one another, are H, alkyl having from 1 to 8 carbon atoms which is terminally substituted by
—NH$_2$, —NHCH$_3$ or —N(CH$_3$)$_2$, or one of the following groups:

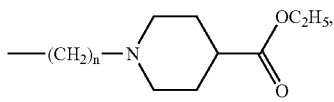

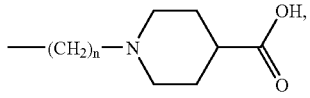

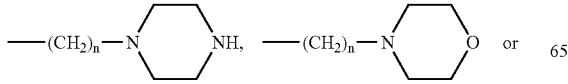

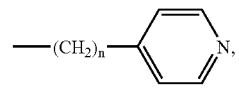

wherein n is an integer of 0–10.

4. A compound according to claim 1 which is of the formula:

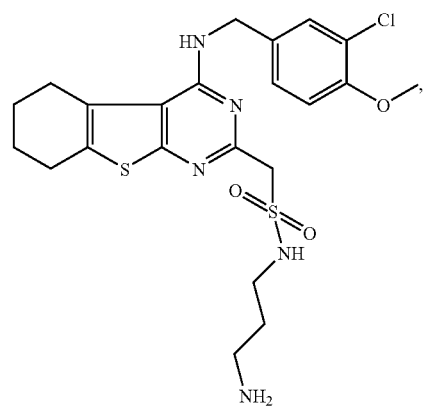

I1

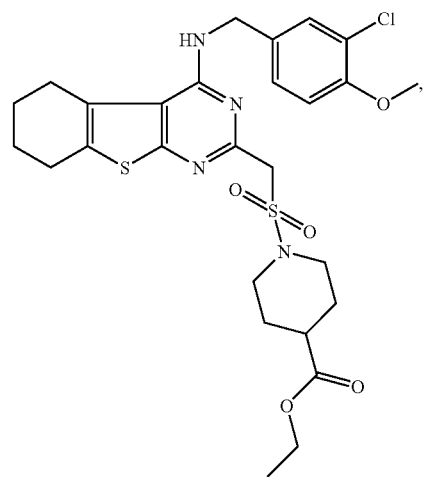

I2

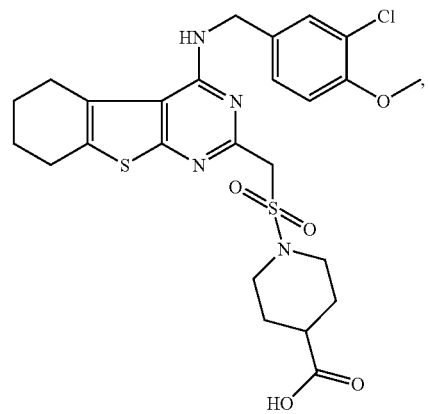

I3

-continued
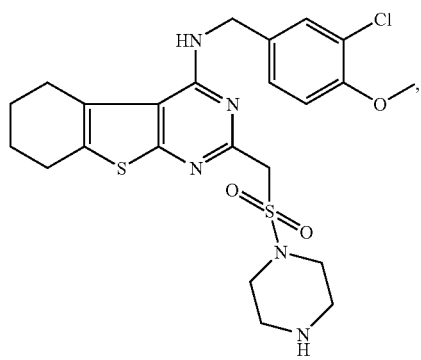
I4
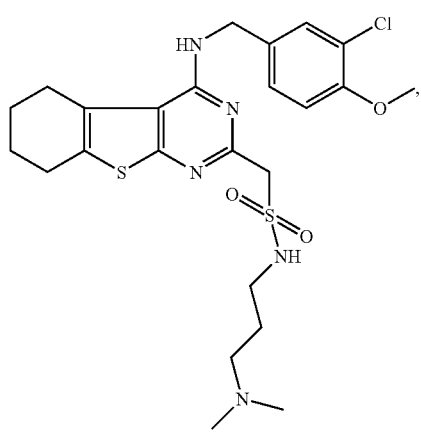
I5
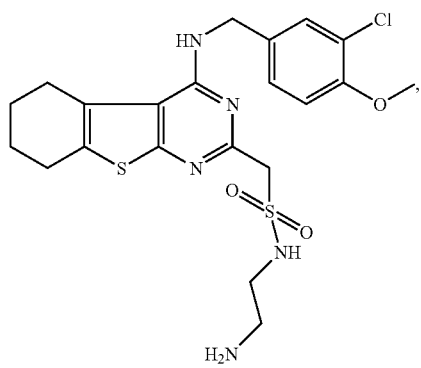
I6
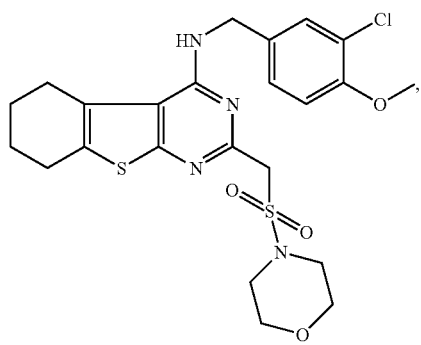
I7
-continued
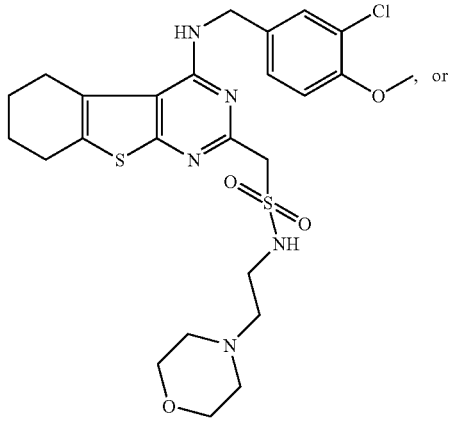
I8
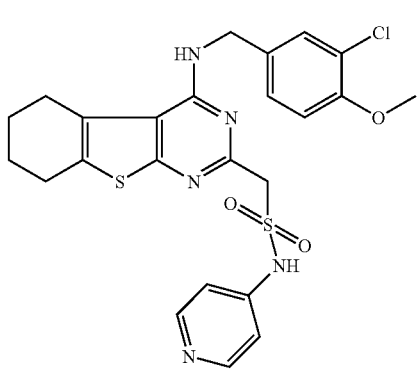
I9
or a physiologically acceptable salt thereof.
5. A process for preparing a compound of the formula I according to claim 1, or a salt thereof,
comprising reacting:
a) a compound of the formula II
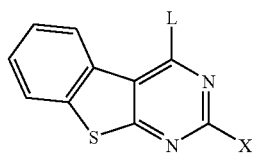
II
wherein
X is —CH$_2$SO$_2$NR$^3$R$^4$, and
L is Cl, Br, OH, SCH$_3$ or a reactive esterified OH group, with a compound of the formula III
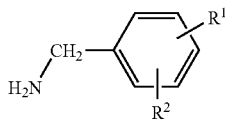
III or b) reacting a compound of the formula IV

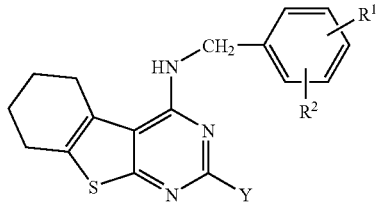

wherein

Y is —CH$_2$SO$_2$Q, and

Q is Cl, Br, OH or a reactive esterified OH group, with a compound of the formula V

HNR$^3$R$^4$ V and/or converting a compound of the formula I into its salt.

6. A compound of the formula II

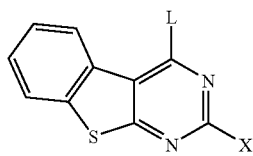

wherein

X is —CH$_2$SO$_2$NR$^3$R$^4$,

L is Cl, Br, OH, SCH$_3$ or a reactive esterified OH group, and

R$^3$ and R$^4$, independently of one another, are H, a heteroaromatic radical, alkyl or alkenyl having 1–10 carbon atoms, each of which is unsubstituted or terminally substituted by —NH$_2$, —NHA$^1$ or —NA$^1$A$^2$ and in which one or two CH$_2$ groups may be replaced by one or more —CH=CH— groups, —O—, —NH— or —NA$^1$—, or R$^3$ and R$^4$ together are cycloalkyl or cycloalkylene having 3–7 carbon atoms, which is unsubstituted, monosubstituted or polysubstituted by —Hal, —NH$_2$, —NHA$^1$, —NA$^1$A$^2$, —NHCOA$^1$, —NHCOOA$^1$, —COOH, —COOA$^1$, —CONH$_2$, —CONHA$^1$, or —CONA$^1$A$^2$ and in which one or two —CH$_2$— groups may be replaced by one or more —O—, —NH—, —NA$^1$—, —NCOA$^1$— or —NCOOA$^1$, A$^1$ and A$^2$ are each, independently of one another, alkyl or alkenyl having 1–10 carbon atoms, each of which may be substituted by 1–5 F and/or Cl atoms, or A$^1$ and A$^2$ together are cycloalkyl or cycloalkylene having 3–7 carbon atoms, in which one CH$_2$ group may be replaced by —O—, —NH—, —NA$^1$—, —NCOA$^1$— or —NCOOA$^1$—, and Hal is F, Cl, Br or I.

7. A compound of the formula IV

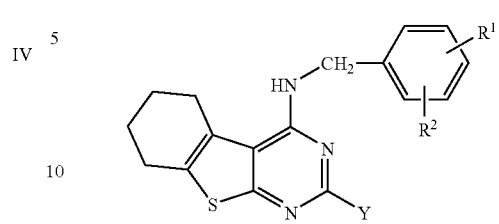

wherein

Y is —CH$_2$SO$_2$Q,

Q is Cl, Br, OH or a reactive esterified OH group, and

R$^1$ and R$^2$ are each, independently of one another, H, OA$^1$, OCOA$^1$, OH or Hal, or R$^1$ and R$^2$ together are alkylene having 3–5 carbon atoms, —O—CH$_2$—CH$_2$—, —CH$_2$—O—CH$_2$—, —O—CH$_2$—O— or —O—CH$_2$—CH$_2$—O—, A$^1$ is, independently, alkyl or alkenyl having 1–10 carbon atoms, each of which may be substituted by 1–5 F and/or Cl atoms, and Hal is F, Cl, Br or I.

8. A process for preparing a pharmaceutical composition, which comprises bringing one or more compounds of the formula I according to claim 1 and/or a physiologically acceptable salt thereof into a suitable dosage form together with at least one solid, liquid or semi-liquid excipient or assistant.

9. A pharmaceutical composition comprising one or more compounds of the formula I according to claim 1 and/or a physiologically acceptable salt thereof, and a pharmaceutically acceptable carrier.

10. A method for treating erectile dysfunction or impotence, comprising administering an effective amount of a compound according to claim 1, or a physiologically acceptable salt thereof, to a patient in need thereof.

11. A method for treating erectile dysfunction, impotence or pulmonary hypertension, comprising administering an effective amount of a compound according to claim 1, or a physiologically acceptable salt thereof, to a patient in need thereof.

12. A pharmaceutical composition comprising one or more compounds of the formula I according to claim 1 and/or a physiologically acceptable salt and at least one further active ingredient.

13. A pharmaceutical composition comprising one or more compounds of the formula I according to claim 1 and/or a physiologically acceptable salt and at least one further active ingredient of:

a) a prostaglandin or prostaglandin derivative,
b) a calcium antagonist,
c) an antithrombotic,
d) an endothelin receptor antagonist,
e) a nitrate,
f) an α-adrenergic inhibitor,
g) a centrally acting dopaminergic active ingredient,
h) an ACE inhibitor,
i) a NEP inhibitor,
j) a mixed α, β-inhibitor, or
k) a vasoactive intestinal peptide.

14. A kit consisting of separate packs of:
(a) an effective amount of a compound of the formula I according to claim 1 and/or a physiologically acceptable salt thereof and
(b) an effective amount of a further active ingredient.

15. A method of treating erectile dysfunction, impotence, or pulmonary hypertension, comprising administering an effective amount of a pharmaceutical composition according to claim 12 to a patient in need thereof.

16. A method of treating pulmonary hypertension comprising administering an effective amount of a compound according to claim 1, or a physiologically acceptable salt thereof, to a patient in need thereof.

* * * * *